United States Patent [19]

Rogers

[11] Patent Number: 5,531,692

[45] Date of Patent: Jul. 2, 1996

[54] SAFETY SYRINGE

[76] Inventor: William D. Rogers, 363 Hill St., Southampton, N.Y. 11968

[21] Appl. No.: 318,966

[22] Filed: Oct. 6, 1994

[51] Int. Cl.[6] ............................................. A61M 5/00
[52] U.S. Cl. ..................... 604/110; 604/164; 604/171; 604/181; 604/187; 604/272
[58] Field of Search ............................. 604/110, 44, 51, 604/52, 93, 117, 158, 162, 164, 171, 181, 187, 192, 194, 195, 196, 239, 264, 272

[56] References Cited

U.S. PATENT DOCUMENTS 4,772,265   9/1988   Walter ........................................ 604/164

*Primary Examiner*—Corrine M. Maglione
*Assistant Examiner*—N. Kent Gring
*Attorney, Agent, or Firm*—Parkhurst, Wendel & Burr

[57] ABSTRACT

A safety syringe including a generally cylindrical needle body having first and second opposite ends, the first end being open, a needle member extending from the second end of the needle body, a plunger having a central bore and piston secured to an end of the plunger, the plunger and piston being inserted through the first end of the needle body, the piston sealingly engaging an inner surface of the needle body, a stylette having a sharp point, the stylette extending through the needle member, penetrating through and frictionally engaging the piston and extending into the central bore of the plunger, wherein the sharp point of the stylette is normally retracted into the needle member to prevent needle-stick injuries, and extends from the needle member upon applying a biasing force to the piston by depressing the plunger, whereby frictional engagement between the piston and the stylette forces the sharp point to be exposed from the needle member.

7 Claims, 3 Drawing Sheets

SAFETY SYRINGE

BACKGROUND OF THE INVENTION

1. Field of the Invention

The present invention is directed to a syringe. More particularly, the invention relates to a safety syringe which prevents needle-stick injuries unless a biasing force is applied to the plunger thereby to expose a sharp point necessary for penetration of tissue.

2. Related Art

Recently, concerns have been raised over protecting medical personnel from coming into contact with infected equipment. Such concerns have lead to the development of safety syringes which protect or shield the sharp point of the needle when not in use, so as to prevent needle-stick injuries from used syringes.

An example of such a syringe is shown in U.S. Pat. No. 5,088,986 which utilizes a needle sheath which is retractable so as to expose a needle for administering medication. The mechanism used to retract the sheath is relatively complex, relying on a switch device and a spring-loaded mechanism.

U.S. Pat. No. 4,969,877 discloses a syringe having a retractable needle. The syringe includes an outer housing having an inner chamber which is slidable therein, the inner chamber having a needle extending therefrom. The syringe is adapted to lock into a retracted position and into a deployed position forwardly within the housing for injection.

U.S. Pat. No. 4,941,883 discloses a syringe which is somewhat similar to that shown in the '877 patent in that a retractable needle is provided. However, use is made of a reservoir which is parallel to a sheath in which the needle retracts. Fluid communication between the needle and the reservoir is achieved through a radial opening and radial apertures, and separate plungers are used for deployment of the needle and injection of medication. Other safety needle apparatuses are shown in U.S. Pat. Nos. 4,834,718 and 4,507,117.

Each of the state of the art safety needles described above has a relatively complex structure, such as spring-loaded switch mechanisms, to protect the sharp point of the needle. Accordingly, while such syringes attempt to offer increased safety, they are costly to manufacture. Additionally, the prior art safety syringes require additional manipulation of the safety devices to ready them for injecting medication. Accordingly, objectives of the present invention include provision of a simple, easy to use and cost-effective safety syringe which is adapted to prevent needle-stick injuries.

SUMMARY OF THE INVENTION

The invention provides a safety syringe having a generally cylindrical needle body, a plunger having a piston inserted into a first end of the needle body, and a needle member extending from the second end of the needle body. Further, a stylette having a sharp point is positioned such that it extends through the needle member, penetrates through and frictionally is engaged by the piston, and extends into a central bore in the plunger. According to this arrangement, only when the user depresses the plunger, the sharp point of the stylette is exposed for penetration of skin. In this regard, when the plunger is depressed, the frictional engagement between the piston and stylette passing therethrough causes the stylette to move with the piston member such that the sharp point of the stylette is exposed.

Preferably, the piston is flexible between biased and unbiased positions, such that upon release of the plunger, the piston returns to its unbiased position to retract the sharp point into the needle member. Thus, the syringe is automatically rendered safe upon release of the plunger.

Preferable embodiments include a side port along an outer surface of the needle member through which medication is released. Additionally, a stop device may be provided to prevent the sharp point of the stylette from extending beyond a predetermined distance from the distal end of the needle member.

DETAILED DESCRIPTION OF THE PREFERRED EMBODIMENTS

Figure 1:
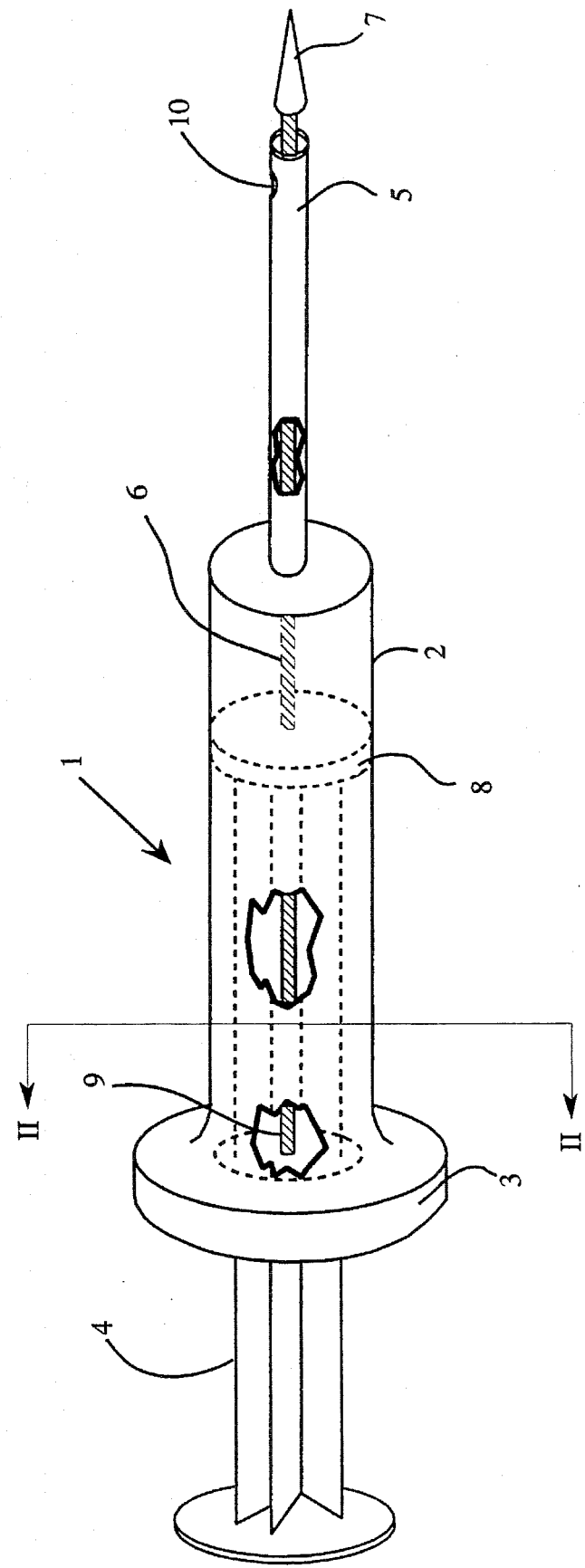
FIG. 1 is a perspective view of the present safety syringe, having cut-away portions to show the extension of the stylette.

FIGS. 1–5 show an embodiment of the present invention not drawn to scale, including safety syringe 1 having needle body 2 which includes a plunger 4 inserted through a first, open end of the needle body, and a needle member 5 extending from a second end of the needle body. Needle body 2 includes handle portion 3 useful for gripping by the user. Additionally, piston member 8 is secured to an end of plunger 4, piston member 8 tightly and frictionally engaging an inner surface of the needle body 2 so as to be in sealing contact therewith.

Figure 2:
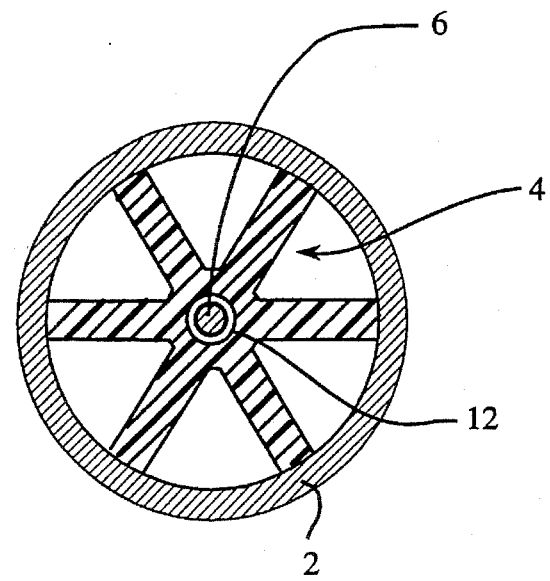
FIG. 2 is a cross-sectional view of section line II—II in FIG. 1.

Of particular importance, stylette 6 extends through needle member 5, penetrates piston member 8 and extends into plunger 4 through axial bore 12 thereof, as shown in FIG. 2. Stylette 6 frictionally engages piston 8 which may be formed of a rubber material, for example.

Stylette 6 bears a sharp point 7 at a distal end thereof, stylette 6 terminating at opposite end 9. Additionally, needle member 5 may include a side port 10 through which the medication flows.

During operation, the user applies a pressing biasing force to plunger 4 to force initial movement of piston 8 through needle body 2, just prior to forcing needle member 5 through tissue of the patient. Because of the frictional engagement between piston 8 and stylette 6, the stylette initially moves in conjunction with the piston 8, so as to force sharp point 7 to protrude from needle 5, as shown in FIG. 1. Appropriate stop means may be provided in the needle member 5 to prevent the sharp point 7 from protruding more than a predetermined distance from needle member 5, discussed in more detail below.

Figure 3:
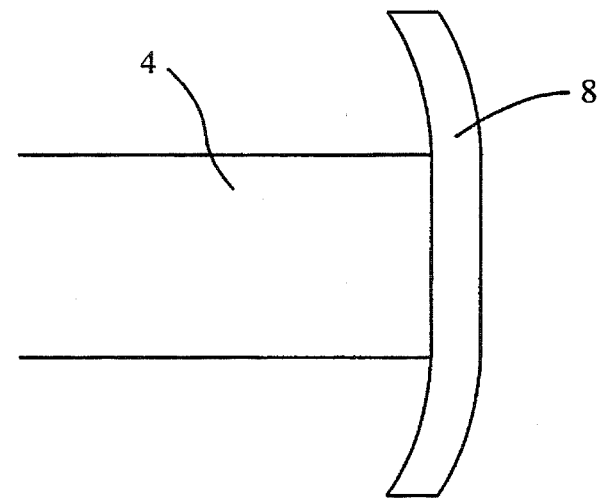
FIG. 3 is a side view showing deformation of the piston of the present safety syringe.

In a preferred embodiment, the piston member 8 is somewhat flexible such that upon applying the pressing biasing force to plunger 4, it deforms as shown in FIG. 3. Accordingly, upon release of the biasing force, the piston returns to its unbiased position, thereby retracting sharp point 7 back into needle member 5. Thus, the present syringe is rendered automatically safe upon releasing plunger 4.

Figure 4:
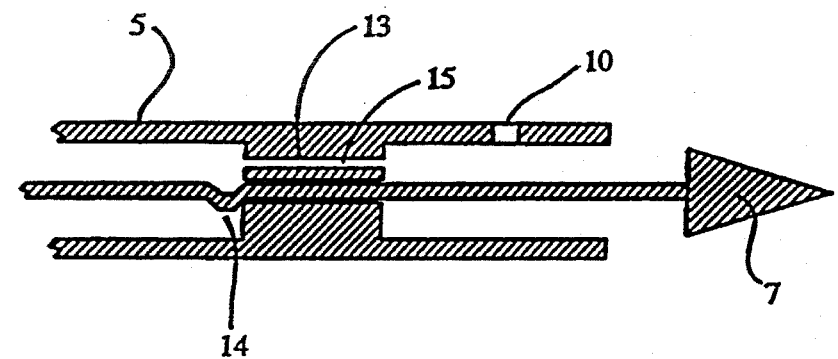
FIGS. 4 and 5 show partial cross-sectional views of the present safety syringe showing stop means.
Figure 5:
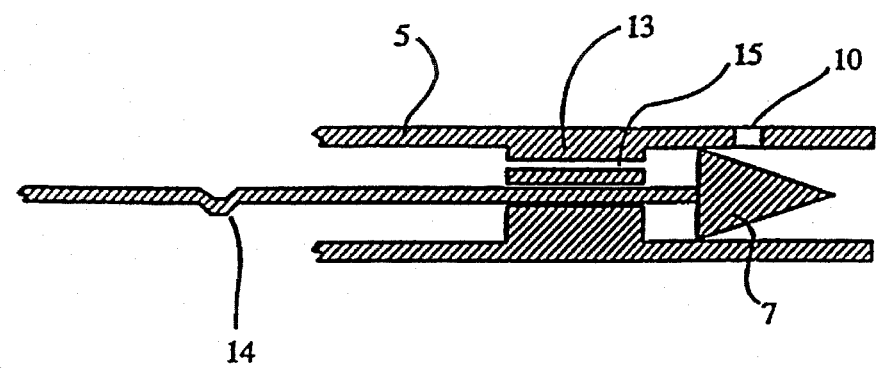

FIGS. 4 and 5 show a particular form of the stop means used to prevent the sharp point 7 from extending too far beyond the end of needle member 5. Crimped portion 14 is provided to abut step 13 having axial througholes 15, as shown in FIG. 4. At that point, axial movement of the stylette 6 is stopped, but piston member 8 continues to slide axially simply by pressing plunger 4 with enough force to overcome the friction between stylette 6 and piston member 8. It is noted that the frictional engagement between piston member 8 and stylette 6 is chosen to be high enough such that sharp point 7 remains exposed during puncturing of tissue of the patient.

The present safety syringe does not impose any material requirements beyond those of a conventional syringe. For example, plunger 4 and needle body 2 may be formed of a suitable plastic material, while piston member 8 may be formed of a suitable rubber material. Stylette 6, needle member 5 and sharp point 7 may be all formed of appropriate surgical-grade metals.

While a particular embodiment has been shown and described, it will be understood that the invention is not limited thereto since many modifications may be made and will become apparent to those skilled in the art without departing from the scope and spirit of the claims which follow.

I claim:

1. A safety syringe, comprising:

a generally cylindrical needle body having first and second opposite ends and an interior volume, said first end being open and said second end having a opening;

a needle member extending from said second end of the needle body and being in communication with said in error volume through said opening;

a plunger having a central bore and piston secured to an end of the plunger, said plunger and piston being inserted through said first end of the needle body, said piston sealingly engaging an inner surface of the needle body;

a stylette having a sharp point, said stylette extending through the needle member, penetrating through and frictionally engaging said piston and extending into the central bore of the plunger, said piston being slidable with respect to and over a length of said stylette, wherein said sharp point of the stylette is normally retracted into the needle member to prevent needle-stick injuries, and extends from the needle member upon applying a biasing force to said piston by depressing said plunger, whereby frictional engagement between the piston and the stylette forces said sharp point to be exposed from said needle member.

2. The safety syringe of claim 1, wherein said piston is flexible between biased and unbiased positions.

3. The safety syringe of claim 1, further comprising a side port along an outer surface of the needle member through which medication is released.

4. The safety syringe of claim 1, further comprising stop means to prevent said sharp point from extending from needle member beyond a predetermined distance.

5. The safety syringe of claim 4, wherein said stop means comprises a step along an inner surface of the needle member and a crimped portion of the stylette which abuts said step.

6. The safety syringe of claim 5, wherein said step is cylindrical.

7. The safety syringe of claim 6, wherein said step contains a plurality of axial flow holes extending therethrough.

* * * * *